(12) United States Patent
Averkiou (10) Patent No.: US 6,494,839 B1
(45) Date of Patent: Dec. 17, 2002

(54) ULTRASONIC DIAGNOSTIC IMAGING SYSTEM TRANSMITTER FOR SUM AND DIFFERENCE FREQUENCY IMAGING

(75) Inventor: Michalakis Averkiou, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 15 days.

(21) Appl. No.: 09/923,597

(22) Filed: Aug. 6, 2001

(51) Int. Cl.[7] ................................................ A61B 8/00
(52) U.S. Cl. ...................................... 600/443; 600/458
(58) Field of Search ................................. 600/437, 440, 600/441–447, 453–458; 128/916; 341/155; 73/599, 602, 625, 626; 367/7, 11, 130, 138

(56) References Cited

U.S. PATENT DOCUMENTS

| 4,012,950 | A | | 3/1977 | Kompfner et al. |
|---|---|---|---|---|
| 5,675,554 | A | | 10/1997 | Cole et al. |
| 5,724,976 | A | | 3/1998 | Mine et al. |
| 5,856,955 | A | | 1/1999 | Cole et al. |
| 5,879,303 | A | | 3/1999 | Averkiou et al. |
| 5,964,708 | A | * | 10/1999 | Freeman et al. ............ 600/447 |
| 6,104,673 | A | | 8/2000 | Cole et al. |
| 6,117,082 | A | | 9/2000 | Bradley et al. |
| 6,172,939 | B1 | | 1/2001 | Cole et al. |

* cited by examiner

Primary Examiner—Marvin M. Lateef
Assistant Examiner—Ali Imam
(74) Attorney, Agent, or Firm—W. Brinton Yorks, Jr.

(57) ABSTRACT

An ultrasonic diagnostic imaging system is described for performing nonlinear echo signal imaging with intermodulation product (sum or difference frequency) components. The system includes a digital transmitter which develops digital waveforms for two frequencies of a transmit beam. The digital waveforms are combined, converted to analog waveforms, and applied as transmit signals to the elements of a transducer array. In an alternate embodiment, a library of digital, multifrequency waveforms is maintained, from which a desired digital waveform is selected, converted to an analog waveform, and applied as transmit signals to the elements of a transducer array.

24 Claims, 8 Drawing Sheets

ULTRASONIC DIAGNOSTIC IMAGING SYSTEM TRANSMITTER FOR SUM AND DIFFERENCE FREQUENCY IMAGING

This invention relates to ultrasonic diagnostic imaging systems and, in particular, to ultrasonic diagnostic imaging systems which transmit different ultrasonic frequencies for ultrasonic sum and difference frequency imaging.

Harmonic imaging is in widespread use in ultrasonic imaging today because of the advantages in signal segmentation and image clarity which it provides. Harmonic imaging at present has two applications: harmonic contrast imaging and tissue harmonic imaging, both of which involve nonlinear signal components. Examples of these two types of harmonic imaging may be found in U.S. Pat. Nos. 5,833,613 (for harmonic contrast) and 5,879,303 (tissue harmonic) of which I am a co-inventor. Harmonic contrast imaging provides the advantage of sharp signal segmentation and signal-to-clutter improvement due to the fact that harmonic contrast agents return relatively strong harmonic signals in response to fundamental frequency insonification. These relatively strong harmonic contrast signals are readily distinguished from the fundamental frequency and relatively low level harmonic signals returned from tissue and other substances in the body. Tissue harmonic imaging, while having a signal-to-noise deficit as compared to fundamental frequency imaging, provides an advantage in image clarity through a reduction in image clutter. Since the distortion of acoustic waves passing through tissue which gives rise to the harmonic components only begins to develop and build as the waves travel deeper into the body, near field scatterers which are a source of image clutter can scatter only the low or insignificant levels of harmonic energy present at shallow depths. Thus, tissue harmonic images will exhibit reduced clutter as compared to fundamental frequency images, although at reduced signal levels due to the lower level of the harmonic components and by reason of depth dependent attenuation of the higher frequency harmonic signals. It would be desirable to utilize nonlinear signals which afford the foregoing advantages but with greater signal levels, better signal-to-clutter ratios, broader bandwidths, and reduced depth dependent attenuation.

In accordance with the principles of the present invention, ultrasonic imaging is performed by transmitting an ultrasound beam with two or more different frequency components. When the beam passes through a nonlinear transmission medium or encounters a nonlinear scatterer the different frequency components intermodulate and develop sum and difference frequencies, which are contained in returning echo signals, detected and used to form an ultrasonic image. In accordance with one aspect of the present invention, a multiple frequency beam transmitter is provided with multiple digital transmit signal generators producing signals of different frequencies which are combined digitally to form a composite transmit signal. In accordance with another aspect of the present invention, composite multiple frequency transmit signals are digitally stored, then selected and converted to analog form for transmission. In accordance with a further aspect of the present invention, the transmitted frequency components are located on opposite sides of the transducer peak response (center) frequency, with a received difference frequency signal located in the vicinity of the peak response point of the transducer characteristic. In accordance with another aspect of the present invention, the amplitudes of the transmitted frequencies are chosen in consideration of the effects of depth dependent attenuation and/or the properties of contrast agent microbubbles.

Figure 1:
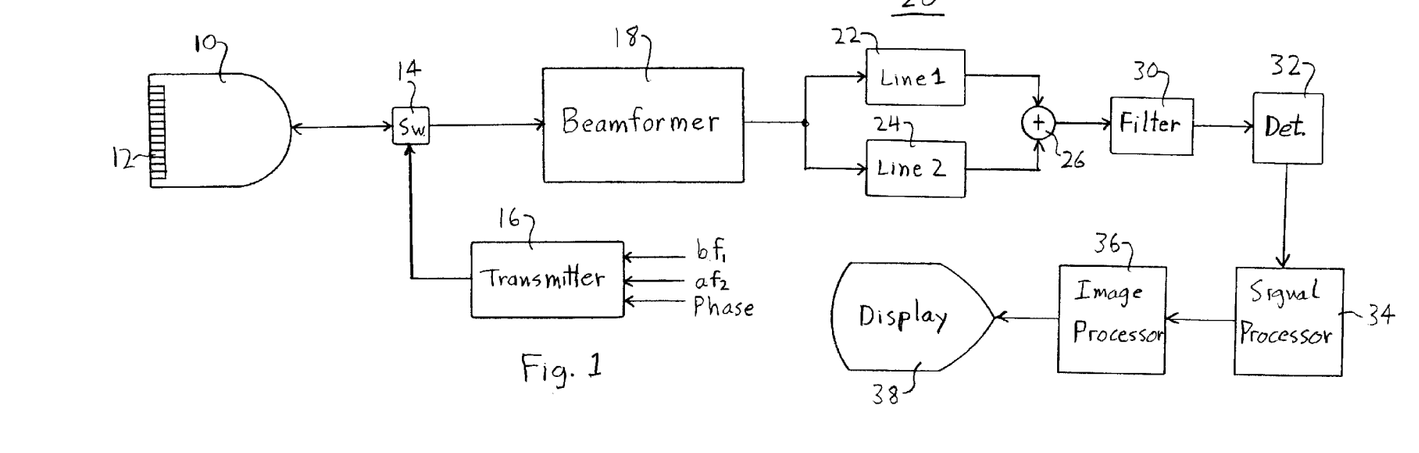
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. This system operates by scanning a region of the body being imaged with ultrasonic transmit beams each having two or more frequency components $f_1$, $f_2$, etc. As each beam is transmitted along its steered path through the body, the multiple frequency components of the beam are intermodulated by the nonlinear effects of the tissue through which the beam passes or the nonlinear response of a contrast agent microbubble encountered by the beam. This intermodulation of the multiple frequency components of the beam produces signal components which are at the sum and difference frequencies of the transmit frequencies, that is, $f_1+f_2$ and $f_1-f_2$. The sum or difference signal components are contained in echoes returned from the body and are used to produce the ultrasonic image of the scanned region.

Sum and difference frequencies have been used in ultrasound systems in the past. These applications have generally involved the simultaneous transmission of two or more beams by separate transducers to a specific target location at which the beams interact with each other to produce sum and difference signals which are then usually detected by a third transducer. In U.S. Pat. No. 3,987,673 an arrangement of this type is used for a Doppler flowmeter to produce Doppler shifted signals at the intersection point with reduced susceptibility to angle of incidence variation. In U.S. Pat. No. 5,601,086 the beat frequencies at the interaction volume of two intersecting beams are used to measure the flow rate of a contrast agent, and in U.S. Pat. No. 5,903,516 the beat force generated at the intersection of two beams generates an acoustic wave that can be detected by a receiver. All of these arrangements require precise aiming of the transmitting transducers so that the beams will intersect at the desired location. They all require multiple transducers, usually two for transmitting and a third for receiving. Furthermore, each transmission only elicits information from a single area in the image field, the area in which the multiple beams intersect. The intersection point must be steered over the entire image field in order to scan the full field. By contrast, an embodiment of the present invention can utilize only a single transmit beam which is steered through the image region in the normal manner and does not have to intersect any other beam. Since only a single beam is necessary, only a single mechanically steered transducer or electronically steered array transducer is needed, although the present invention can also be practiced with multiple transducers if desired. Furthermore, as the beam travels through the body along its beam path, the sum and difference signal components of the different frequency components of the beam are reflected from points in the body all along the beam path, enabling a full scanline of image information to be acquired by each transmission, rather than just information from a single area of the image field.

An embodiment of the present invention can make efficient use of the finite bandwidth of the scanhead transducer used for imaging. In harmonic imaging of tissue and contrast agents, the transmit and receive bands must both be contained within the transducer passband so that the single transducer scanhead can be used for both transmission and reception of the differing transmit and receive bands. As shown in my U.S. Pat. No. 5,879,303 in FIGS. 7 and 8, this generally results in the transmit band being located at the lower end of the transducer passband and the receive band being located at the upper end of the transducer passband. Unlike fundamental frequency imaging, where the identical transmit and receive bands are both located in the center of the transducer passband where response is optimal, neither of the operative bands is at the center of the transducer band.

Figure 3:
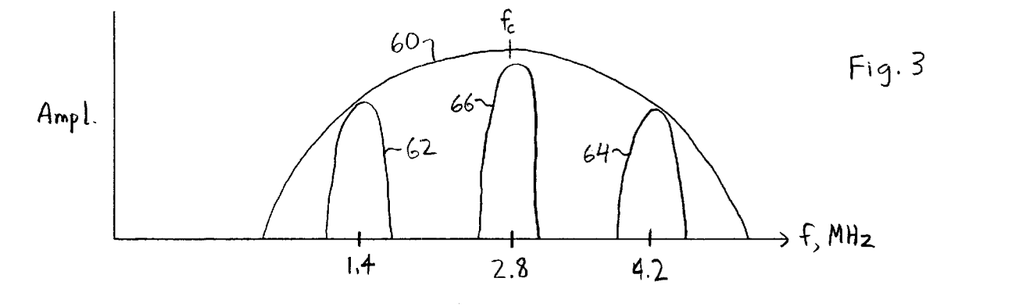
FIG. 3 illustrates the transmit and receive bands of a transducer operated in accordance with the present invention.

An embodiment of the present invention can overcome this problem of suboptimal response. FIG. 3 illustrates a representative transducer passband 60. In this example the transducer is transmitting a beam with two transmit bands 62 and 64, one located at 1.4 MHz and another located at 4.2 MHz. As the beam passes through the tissue of the body, and when it encounters a contrast agent microbubble, the nonlinear effects of these substances cause the two frequencies of the transmit beam to mix or intermodulate and produce sum and difference frequencies in the manner of a parametric array, which are returned in echoes of the transmit beam. In the example of FIG. 3, the difference frequency of the two transmit frequencies is (4.2−1.4), which is 2.8 MHz as shown by the receive band 66. As the passband 60 shows, this echo frequency falls at or around the center of the transducer passband, where the transducer exhibits its most sensitive response. Thus, the transmit frequencies are located at the upper and lower portions of the transducer passband, but for transmission the passband rolloff is acceptable due to the power level of the transmit beam. The received echoes are many dB lower in intensity than the transmit beam, and are advantageously received at the most sensitive region of the transducer passband.

Figure 4:
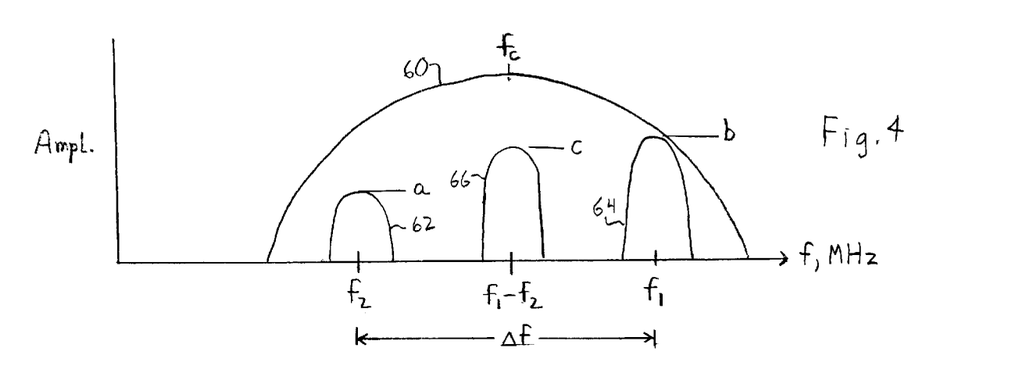
FIG. 4 illustrates some of the variable transmit parameters of a multifrequency transmitter of the present invention.

FIG. 1 utilizes a transmitter 16 which transmits multifrequency beams for the nonlinear generation of sum and difference signals within the body. The transmitter is coupled by a transmit/receive switch 14 to the elements of an array transducer 12 of a scanhead 10. The transmitter is responsive to a number of control parameters which determine the characteristics of the transmit beams, as shown in the drawing. FIG. 4 illustrates these parameters spectrally in relation to the passband 60 of the transducer 12. The two frequencies $f_1$ and $f_2$ of the multifrequency beam are controlled, which determines the frequency differential $\Delta f$ between the two frequency components of the beam, as well as the frequencies at which the sum $(f_1+f_2)$ and difference $(f_1-f_2)$ frequency components will fall. Also controlled are the amplitudes or intensities a and b of the two transmitted frequency components, causing the transmit beam to be of the form $(b\sin(2\pi f_1 t)+a\sin(2\pi f_2 t))$. The received difference signal component $(f_1-f_2)$ will have an amplitude c as illustrated by the size of band 66 in FIG. 4. This amplitude c is not a linear product of the a and b intensities, however, as the sum and difference signals result from nonlinear effects.

Figure 5:
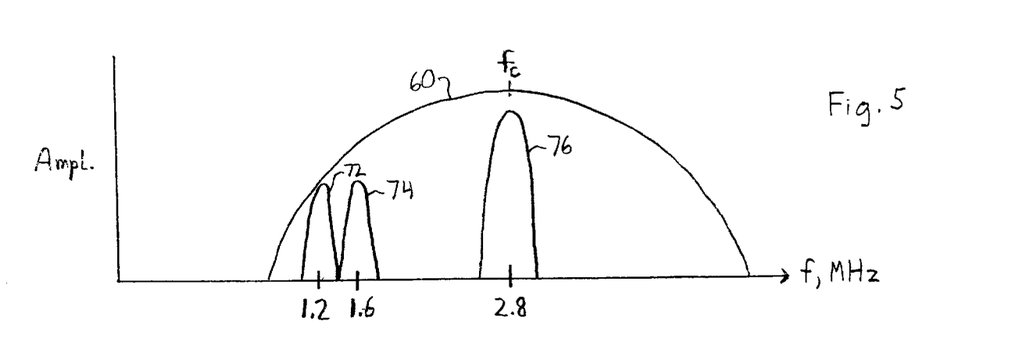
FIG. 5 illustrates another set of transmit and receive bands of a transducer operated in accordance with the present invention.

FIG. 5 illustrates an embodiment of the present invention which utilizes sum signal components. In this example the transmit beam includes two frequency bands 72 and 74 located at 1.2 MHz and 1.6 MHz. These transmit frequency components are nonlinearly intermodulated or mixed to result in an echo sum signal band 76 located at 2.8 MHz. The transmit frequencies will also have a difference component of 0.4 MHz which is below the lower cutoff of the transducer passband 60. The sum components 76 are seen to fall at the center of the transducer passband 60 and are used for imaging by the ultrasound system.

Figure 2A:
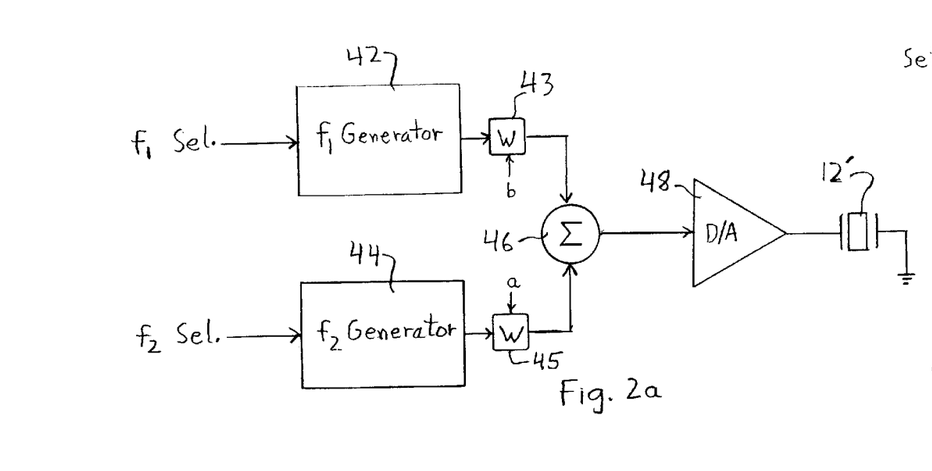
FIGS. 2a and 2b illustrate two beam transmitters suitable for use in the embodiment of FIG. 1.
Figure 2B:
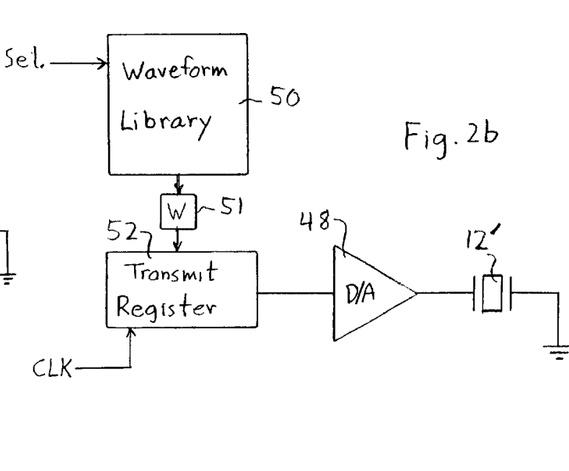

Returning to FIG. 1, the transducer array 12 receives echoes from the body containing sum and difference frequency components which are within the transducer passband. These echo signals are coupled by the switch 14 to a beamformer 18 which appropriately delays echo signals from the different elements then combines them to form a sequence of sum and/or difference signals along the beam from shallow to deeper depths. Preferably the beamformer is a digital beamformer operating on digitized echo signals to produce a sequence of discrete coherent digital echo signals from a nearfield to a farfield depth of field. The beamformer may be a multiline beamformer which produces two or more sequences of echo signals along multiple spatially distinct receive scanlines in response to a single transmit beam. The beamformed echo signals are coupled to a nonlinear signal separator 20. The separator 20 may be a bandpass filter which passes a sum or difference passband 66, 76 to the relative exclusion (attenuation) of the transmit bands 62, 64 or 72, 74. In the illustrated embodiment the separator 20 is a pulse inversion processor which separates the nonlinear signals including the sum and difference components by the pulse inversion technique. Since the sum and difference frequency signals are developed by nonlinear effects, they may advantageously be separated by pulse inversion processing. For pulse inversion the transmitter has another variable transmit parameter which is the phase of the transmit pulse as shown in the drawing. The ultrasound system transmits two or more beams of different transmit polarities or phases. For the illustrated two pulse embodiment, the scanline echoes received in response to the first transmit pulse are stored in a Line1 buffer 22. The scanline echoes received in response to the second transmit pulse are stored in a Line 2 buffer 24 and then combined with spatially corresponding echoes in the Line1 buffer by a summer 26. Alternatively, the second scanline of echoes may be directly combined with the stored echoes of the first scanline without buffering. As a result of the different phases or polarities of the transmit pulses, the out of phase fundamental (linear) echo components will cancel and the nonlinear sum and difference components, being in phase, will combine to reinforce each other, producing enhanced and isolated nonlinear sum and/or difference frequency signals. The sum and difference frequency signals may be further filtered by a filter 30 to remove undesired signals such as those resulting from operations such as decimation. The signals are then detected by a detector 32, which may be an amplitude or phase detector. The echo signals are then processed by a signal processor 34 for subsequent grayscale, Doppler or other ultrasound display, then further processed by an image processor 36 for the formation of two dimensional, three dimensional, spectral, parametric, or other display. The resultant display signals are displayed on a display 38. FIGS. 2a and 2b illustrate two detailed embodiments of the transmitter 16 of FIG. 1. In the embodiment of FIG. 2a, the waveforms for the different frequency components of the transmit pulse are formed separately in digital operations, then combined to form a composite multifrequency transmit signal for application to a transducer element. An f, generator 42 produces the $f_1$ transmit signal component and an $f_2$ generator 44 produces the $f_2$ transmit signal component. The generators produce their respective transmit waveforms in response to input control parameters such as $f_1$ Sel. and $f_2$ Sel. shown in the drawing which determine the $f_1$ and $f_2$ frequency components of the transmitted beam. Other variable input parameters (not shown) may be intensity parameters a and b, and phase or polarity parameters for pulse inversion transmit signals. Alternatively, the output waveforms produced by the generators 42 and 44 may be varied in amplitude and phase or polarity before or after being combined by a combiner 46 into a composite transmit pulse which contains the multiple transmit frequency components. In FIG. 2a the waveforms produced by the generators are weighted by digital weighting processor circuits 43 and 45 which apply the weighting factors a and b to the generated waveforms. The weighting circuits can take the form of digital multipliers and the sign of the weighting factor (+1, −1) can be used to control the polarity of the output waveform. The composite transmit pulse is applied to a D/A converter 48 for conversion to an analog signal, which may be further amplified and filtered as desired and used to drive a transducer element 12'.

FIG. 2b illustrates a second transmitter embodiment in which the composite multifrequency transmit signals are produced in advance, then stored in a waveform library 50, which may be in the form of a digital memory. When a certain multifrequency transmit pulse is desired it is selected from the library 50, weighted by a weighting circuit 51, and stored in a transmit register 52. When the transmitter is triggered to transmit the beam the composite multifrequency waveform is shifted out of the transmit register 52 by a clock signal CLK, converted to an analog signal by the D/A converter 48 and applied to the transducer element 12'. The amplitude of the transmit pulse may be varied by either a digital multiplier preceding the A/D converter such as one used in the weighting circuit, or by an analog amplifier following the A/D converter, and may be filtered in either the analog or digital domain as desired. The individual frequency components may not be separately adjusted in amplitude following the transmit register 52 as the waveform is already a composite at that point in this embodiment.

It will be appreciated that the beam transmitted by the transducer array is steered in a desired beam direction and focused at a desired depth of focus, both of which are effected by the timing of application of transmit waveforms to different elements of the transducer array. Accordingly a number of transmit channels such as those shown in FIGS. 2a and 2b are employed in the transmitter, one for each differently timed transmit waveform. The transmit channels may use the same transmit waveform but the times at which the waveforms of the channels are applied to the transducer elements are varied by the time delay profile needed for steering and focusing from the active elements of the transmit aperture.

Figure 6A:
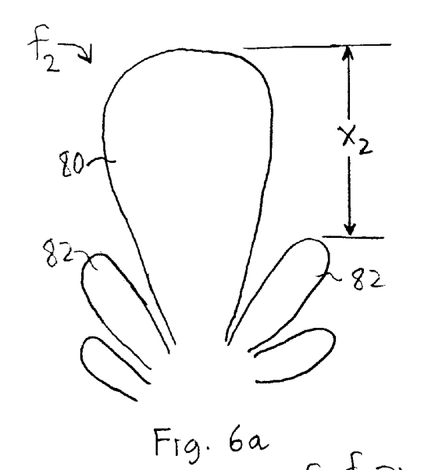
FIGS. 6a–6d illustrate beam patterns of another embodiment of the present invention.
Figure 6B:
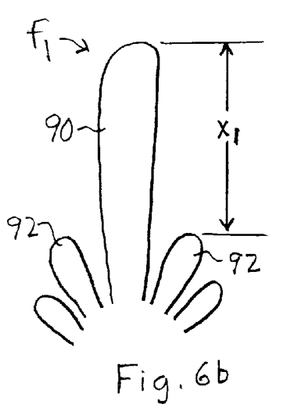
Figure 6C:
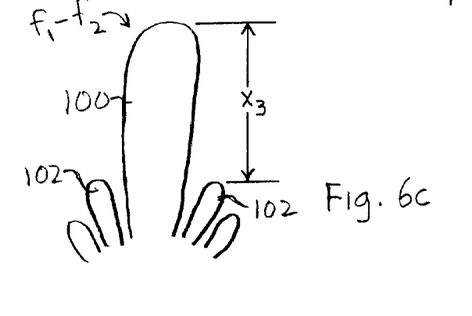

An embodiment of the present invention can provide improved lateral resolution and reduced clutter by virtue of the differing beam profiles of the various frequency components. This is illustrated by the beam profiles of FIGS. 6a–6d. FIG. 6a illustrates a beam profile for a lower $f_2$ frequency component having a relatively broad main lobe 80 and sidelobes 82. The sidelobes, which are a source of clutter as explained in my '303 patent, are $x_2$ dB below the peak of the main lobe as shown in the drawing. FIG. 6b illustrates a beam profile for a higher $f_1$ frequency component. The main lobe 90 of the $f_1$ frequency component is relatively narrower than that of the $f_2$ frequency component by virtue of the higher $f_1$ frequency. In this illustration the sidelobes 92 are $x_1$ dB below the main lobe level and for purposes of this example it is assumed that $x_1=x_2$. FIG. 6c illustrates a beam profile for a resultant sum or difference signal component, in this case, the difference frequency component of $f_1-f_2$. Since this beam profile is a product of the two components of FIGS. 6a and 6b and is for a frequency greater than the $f_2$ frequency in this example, the main lobe 100 of the difference frequency is relatively narrower than the $f_2$ main lobe 80. Furthermore the sidelobes 102 which are a source of clutter are $x_3$ dB below the level of the main lobe 100 where $x_3>x_1=x_2$. Thus there is an improvement in resolution and clutter performance over the use of the low frequency beam component alone. There is also an improvement in penetration over the high frequency component due to the reception at the lower difference frequency.

Figure 6D:
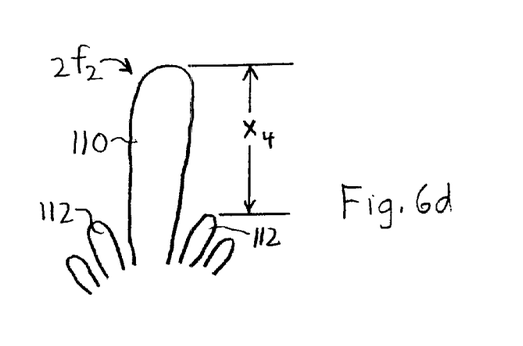
Figure 7:
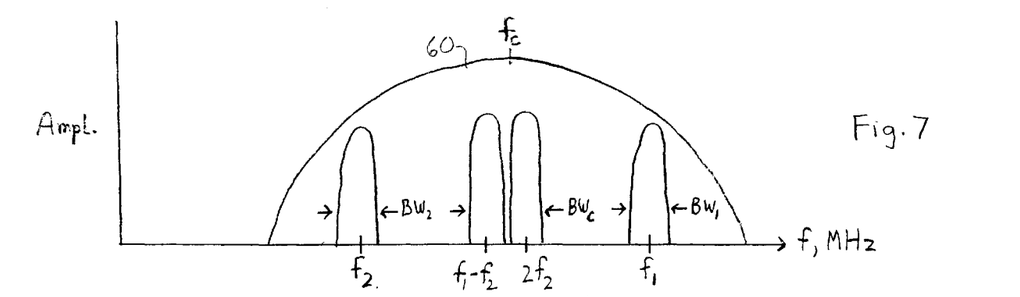
FIG. 7 illustrates another embodiment of the present invention which uses both intermodulation product signals and second harmonic signals.

FIGS. 7–9 illustrate embodiments which combines the benefits of both parametric array difference imaging, harmonic imaging and sum frequency imaging. In the embodiment of FIG. 7 the transmit beam includes a high frequency component $f_1$ exhibiting a band $BW_1$, and a low frequency component $f_2$ exhibiting a band $BW_2$. The frequencies of the transmit beam are chosen so that two types of nonlinearly developed components will be located in the vicinity of the center of the transducer passband 60: difference frequency components ($f_1-f_2$) and second harmonic components $2f_2$ of the lower transmit frequency $f_2$ as shown in this example, and/or a subharmonic of the upper transmit frequency such as ½$f_1$. While each of these nonlinear components will exhibit its own relatively narrow band, careful selection of the transmit frequencies can result in a combined receive band $BW_c$ which is broader than the transmitted bands. This means that the echo passband will be more broadband in nature for better signal resolution, and that the echo signals will exhibit an improved signal-to-noise level since they are a combination of both nonlinear effects. The received echo signals of this embodiment will also exhibit enhanced resolution and clutter performance as illustrated by FIG. 6d, which shows a main lobe 110 and sidelobes 112 for a harmonic echo component $2f_2$. As my '303 patent explains the harmonic beam profile will exhibit improved clutter and signal-to-noise performance as the sidelobes 112 are $x_4$ dB below the level of main lobe 110, where $x_4 > x_1 = x_2$, which is especially beneficial in cases of highly inhomogeneous aberrating tissue layers. Thus, the resultant echo signals can exhibit improved performance where $x_3 \geq x_4 > x_1$, $x_2$ and the signal-to-noise performance of the difference beam profile is $X_3$ dB. It is seen therefore that the embodiment of FIG. 7 combines the performance benefits of both parametric and harmonic imaging in a broadband imaging embodiment.

Figure 8:
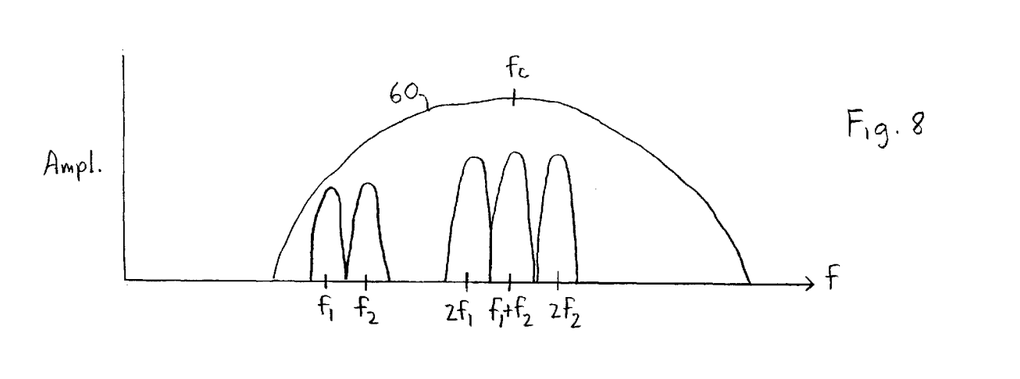
FIG. 8 illustrates an embodiment of the present invention which uses nonlinear sum and harmonic components to reduce the problem of depth dependent attenuation.

One of the problems which harmonic imaging presents is the attenuation of high frequency harmonics as the high frequency signals pass through tissue. This depth dependent attenuation limits the signal penetration and hence the image depth during harmonic imaging. In the embodiment of FIG. 8, a combination of harmonic and sum frequency imaging is used to address this problem. The transmit beam includes transmit frequency components $f_1$ and $f_2$ as shown in the drawing. These components are at the lower portion of the transducer passband 60 and their low frequencies provide good depth penetration in tissue. During reception three echo signal bands are received in the central, more sensitive portion of the transducer passband 60: a harmonic $2f_2$ of the $f_2$ transmit component, a sum signal $f_1+f_2$, and a harmonic $2f_1$ of the $f_1$ transmit component. Each of these bands is progressively lower in frequency than the previous band, resulting in progressively better depth penetration with each band. The three echo signal bands can be received throughout the depth of the image, or they can be selectively used over different depths to produce an image which is a blend of harmonic and sum echo signal components. For example, echo signals in the $2f_2$ band can be received to form the image at shallow depths, the sum signals in band $f_1+f_2$ can be used to produce the image an intermediate depth, and the $2f_1$ signal band can be used to form the image at the deepest image depths, thereby taking advantage of the relative penetration performance of each band. To reduce noise a tracking filter can be employed which moves from a passband encompassing the $2f_2$ band as echoes are initially received at shallow depths, then moves progressively lower as echoes are received from a beam at greater and greater depths. An example of frequencies which may be employed for $f_1$ and $f_2$ in a constructed embodiment of FIG. 8 are 1.2 MHz and 1.6 MHz, resulting in receive signal bands at 3.2 MHz, 2.8 MHz, and 2.4 MHz.

Figure 9:
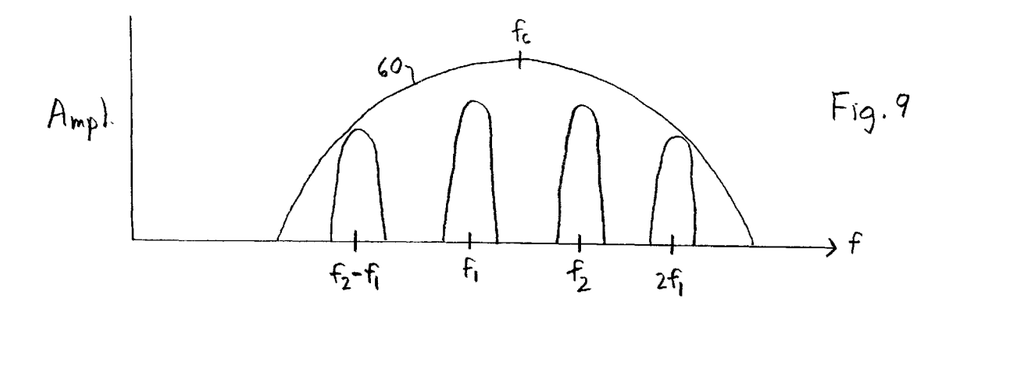
FIG. 9 illustrates an embodiment of the present invention which uses nonlinear difference and harmonic components to reduce the problem of depth dependent attenuation.

FIG. 9 illustrates an embodiment which addresses the problem of depth dependent attenuation by using a combination of harmonic and difference frequency echo signals. The transmit beam in this drawing contains frequency components $f_1$ and $f_2$ as shown. The received echo signals include signals in band $2f_1$, the harmonic of the transmit frequency $f_1$, and signals in band $f_2-f_1$, the difference frequency band. The $2f_1$ high frequency signals are used to produce the near field (shallow depth) portion of the image, providing the clutter reduction which is characteristic of harmonic imaging. Since the $2f_1$ high frequencies are more greatly affected by depth dependent attenuation, the far field (greater depth) portion of the image is formed from the low frequency $f_2-f_1$ difference frequency signals. A variation is to use a blend of both the high and low frequencies in an intermediate range between the near and far field depths. As in the previous embodiment a tracking filter could be used to move the receive signal passband from higher to lower frequencies as the echo signals are received from ever increasing depths to reduce noise in the image. An example of frequencies which may be employed for $f_1$ and $f_2$ in a constructed embodiment of FIG. 9 are 3.0 MHz and 5.0 MHz, resulting in the harmonic signals being located in a 6.0 MHz band and the difference frequency signals in a 2.0 MHz band.

Furthermore, the parametric and harmonic echo components, both being formed by nonlinear processes, may both be advantageously separated from the transmitted signal components in the previous embodiments by either bandpass filtering or, preferably, the pulse inversion technique. This is shown by echoes resulting from two multifrequency transmit beams which differ in phase by 180° ($\pi$):

(+): $\sin\omega_1 t + \sin\omega_2 t$ and
(−): $\sin(\omega_1 t + \pi) + \sin(\omega_2 t + \pi)$ where the two transmit frequencies are $\omega 1t$ and $\omega 2t$ and (+) and (−) indicate the phase difference between the two beams. When the echo signals from the two beams are combined by the pulse inversion technique to separate the second harmonic components the following results: $\sin(\omega_1 t + \pi) = -\sin\omega_1 t$, and therefore the combination of both echoes is $\sin\omega_1 t - \sin\omega_1 t = 0$, which cancels the fundamental transmit component $\omega_1 t$. The harmonic components of the two echoes are $\sin 2\omega_1 t$ and $\sin(2\omega_1 t + 2\pi) = \sin 2\omega_1 t$, which combine to produce $2\sin 2\omega_1 t$, the separated second harmonic of $\omega_1 t$. When the two echoes are combined to produce difference signals, the following results:

$\sin(\omega_1 t - \omega_2 t - \omega_2 t)$ and
$\sin(\omega_1 t + \pi - \omega_2 t - \pi) = \sin(\omega_1 t - \omega_2 t)$ which combine to produce the result of $2\sin(\omega_1 t - \omega_2 t)$. Thus, the parametric difference signal is, like the pulse inversion separated harmonic, enhanced to twice the level of the desired component in a single echo signal. The embodiments of FIGS. 7, 8, and 9, when utilized with pulse inversion separation, thus provide the enhanced benefits of both parametric and harmonic imaging.

Figure 10A:
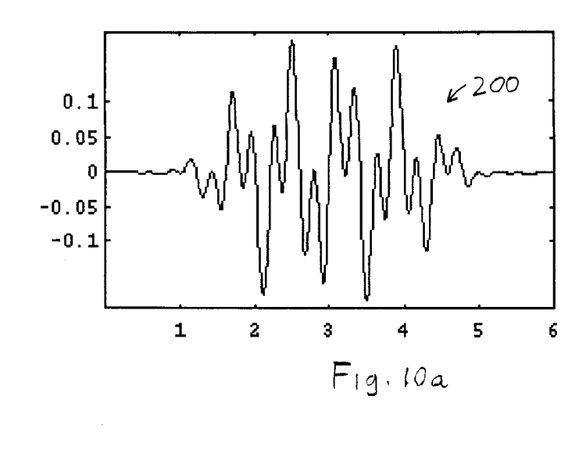
FIGS. 10a and 10b illustrate a multifrequency transmit pulse waveform and a spectrum of that pulse.
Figure 10B:
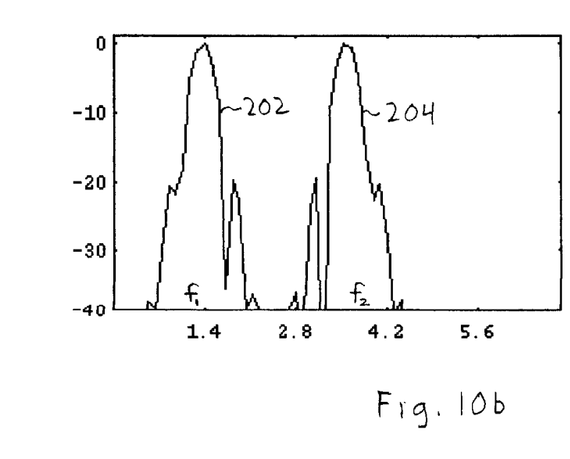

An exemplary acoustic pressure pulse 200 which may be employed in an embodiment of the present invention is shown in FIG. 10a. The spectrum of this transmit pulse is shown in FIG. 10b and has two components $f_1$ and $f_2$ as shown by bands 202 and 204, located about frequencies of 1.4 MHz and 3.6 MHz in this example. When the multifrequency pulse 200 is transmitted in a nonlinear medium such as microbubbles or tissue the nonlinear response will have components that are harmonics of the fundamental transmit bands: $f_1$, $2f_1$, $3f_1$, etc. and $f_2$, $2f_2$, $3f_2$, etc. The nonlinear response will also have components of the sum and difference frequencies of the transmit pulse and their harmonics: $f_1+f_2$, $2(f_1+f_2)$, $3(f_1+f_2)$, etc. and $f_2-f_1$, $2(f_2-f_1)$, $3(f_2-f_1)$, etc. The harmonic beam has the characteristics described above which make it more desirable than the fundamental frequency beam for many applications, including narrower beam-width, lower sidelobes, and less aberration artifacts due to the cumulative generation process which gives rise to the harmonic components. The difference frequency beam is also formed by the cumulative generation process and enjoys many of the same benefits as the harmonic beam, and in addition generally exhibits lower sidelobes and a lower absorption characteristic than the harmonic beam.

Figure 11A:
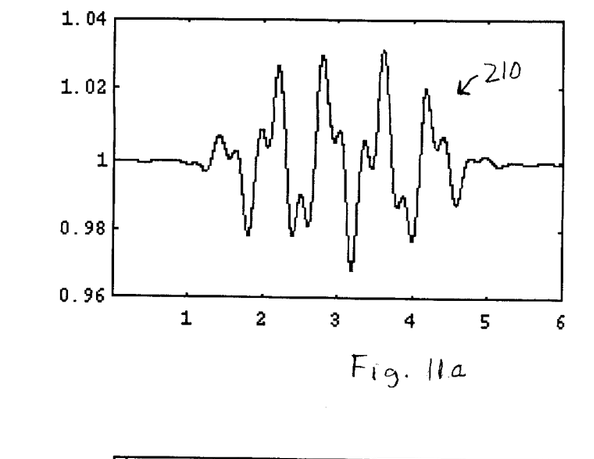
FIGS. 11a and 11b illustrate a low amplitude (low nonlinearity) microbubble response to the pulse of FIG. 10a and the spectrum of the echo returned by that response.
Figure 11B:
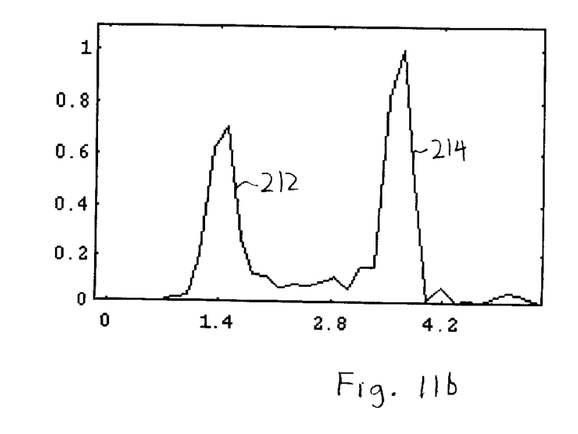

When the acoustic pulse 200 is used to insonify microbubbles at low amplitudes which are insufficient to cause nonlinear bubble oscillation, the oscillation of the bubble radius will appear similar to that shown by curve 210 in FIG. 11a. This example assumes that the microbubble is a 3.2 μm microbubble in blood which is insonified by a pressure of 0.01 MPa. The echo returned by the microbubble will be linear in nature and have a frequency content with two spectral peaks 212, 214 as shown in FIG. 11b, which closely resembles the spectrum of the transmit pulse shown in FIG. 10b, and also the bubble linear resonance characteristic.

Figure 12A:
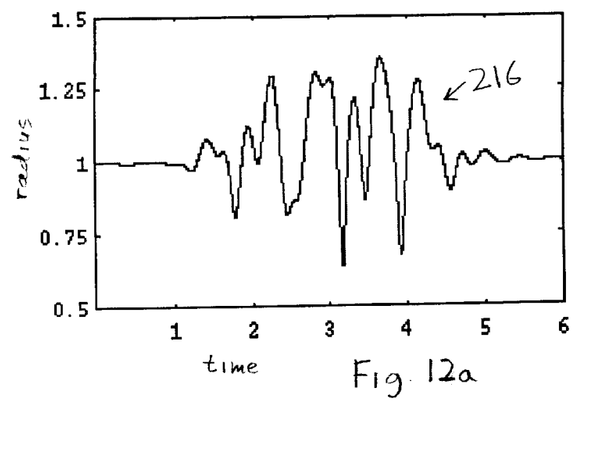
FIGS. 12a and 12b illustrate echoes from a nonlinear microbubble response to the pulse of FIG. 10a and its spectrum.
Figure 12B:
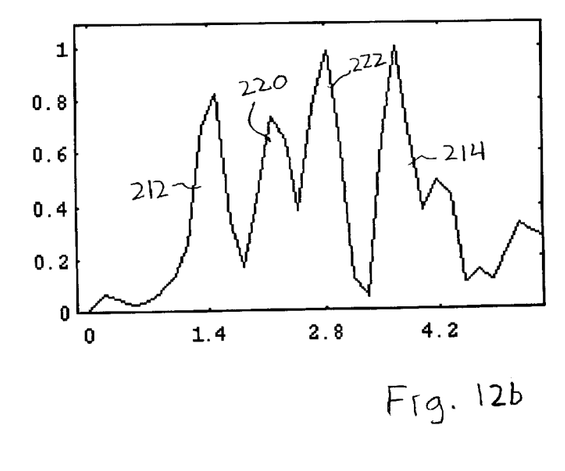
Figure 13:
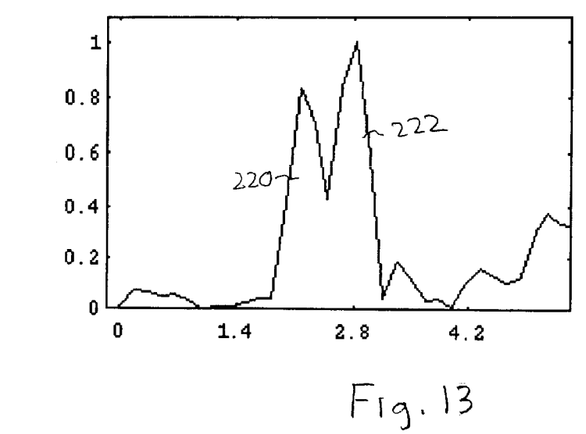
FIG. 13 illustrates the nonlinear portion of the spectrum of FIG. 12b which is separated by pulse inversion processing.

When the amplitude of the transmitted acoustic pulse is increased so that nonlinear bubble behavior results, the radius of the microbubble will oscillate nonlinearly as illustrated by the radius-time curve 216 in FIG. 12a. In this example the acoustic pressure is assumed to be 0.1 MPa. The spectrum of the echo returned by the microbubble is shown in FIG. 12b. This spectrum includes the two transmitted frequency components in bands 212 (where $f_1$=1.4 MHz) and 214 (where $f_2$=3.6 MHz). The spectrum also includes a peak 222 at the second harmonic of $f_1$ (where $2f_1$=2.8 MHz) and a peak 220 at the difference frequency between $f_1$ and $f_2$ (where $f_2-f_1$=(3.6−1.4)=2.2 MHz). When two echoes are obtained from transmit pulses of opposite phase or polarity and combined, the odd harmonics including fundamental frequencies are eliminated, leaving only the even harmonics and sum and difference frequencies in bands 220, 222 as shown in FIG. 13.

Figure 14A:
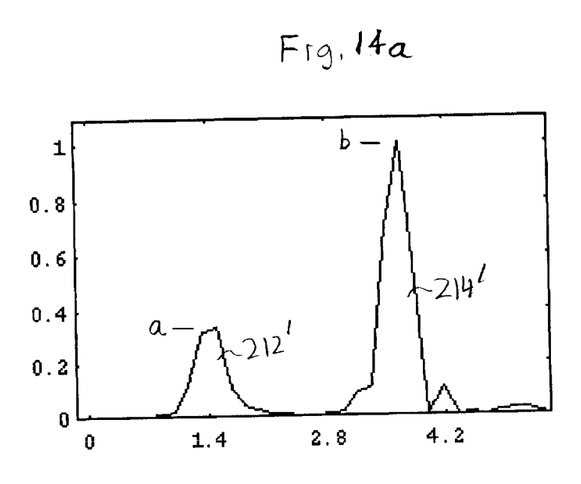
FIGS. 14a and 14b illustrate the spectra of transmit pulses designed for microbubbles of two different sizes.
Figure 14B:
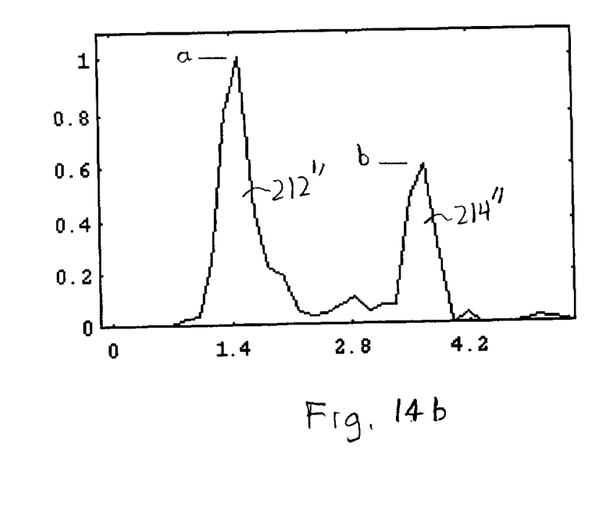

Another advantage of the present invention when used with contrast agents is that the multiple transmit frequencies will excite microbubbles of multiple sizes. Most contrast agents in present use have microbubbles with diameters of 1–10 μm. Smaller bubbles respond better to higher frequency excitation pulses and larger bubbles respond better to lower frequencies. The amplitudes of the respective frequency components of the transmit pulse can therefore be chosen to preferentially excite microbubbles of a given size or range of sizes. This is done by the choice of coefficients a and b in the expressions shown above. For example, FIGS. 14 show spectra of echoes from microbubbles with different sizes when insonified with pulses containing two frequency components as shown in FIG.S 10a and 10b. In this example small (linear) amplitude relationships are used for simplicity of illustration. In FIG. 14a the response of a 1 μm microbubble is shown, whereas in FIG. 14b a 4 μm bubble response is illustrated. The smaller bubble of FIG. 14a has a larger response 214' at the higher frequency and a smaller response 212' at the lower frequency. The larger bubble of FIG. 14b has a larger response 212" at the lower frequency and a smaller response 214" at the higher frequency. When a broad range of frequencies is transmitted, a broad range of bubble sizes will be excited. When used for tissue harmonic imaging rather than contrast agents, where there are no bubbles, the higher band 214' can be of a greater transmit intensity than the lower band 212' to offset the effects of depth dependent frequency attenuation, which attenuates higher frequencies to a greater degree than lower frequencies. Different ratios of coefficients a and b for the $f_1$ and $f_2$ transmit components can be used for different depth zones or a multiple transmit zone focus embodiment. For example the a coefficient for the high frequency component can remain constant or decline with depth while the b coefficient for the low frequency component is increased with depth or deeper zones. These amplitude variations for high and low frequency components can be used individually or together in a particular embodiment.

Figure 15A:
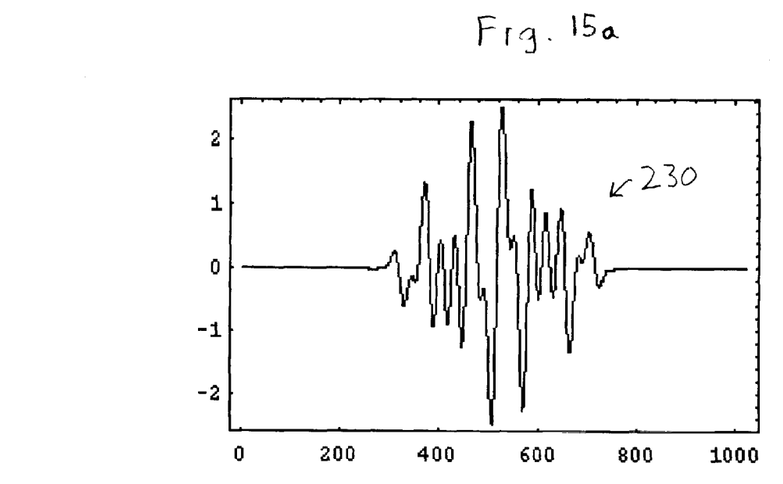
FIGS. 15a and 15b illustrate a pulse waveform for a three frequency transmit beam and the spectrum of the pulse.
Figure 15B:
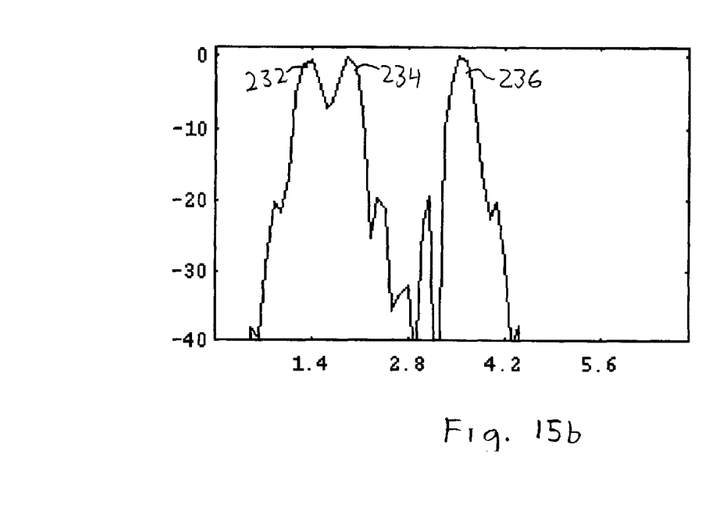

FIGS. 15a and 15b illustrate a transmit pulse waveform 230 and spectrum for a multifrequency transmit beam having three frequency components. As the spectrum of FIG. 15b illustrates, the pressure pulse of FIG. 15a has three frequency peaks 232, 234, and 236, located at $f_1$=1.4 MHz, $f_2$=2.0 MHz, and $f_3$=3.6 MHz. These transmit frequency components will produce nonlinear echo components including:

$f_3-f_2$=1.6 MHz
$f_3-f_1$=2.2 MHz
$2f_1$=2.8 MHz
$f_1+f_2$=3.4 MHz and
$2f_2$=4.0 MHz, all of which can be encompassed within the transducer passband 60. Thus, it is seen that a multifrequency transmit pulse of three constituent frequency components can result in a received echo signal of broad bandwidth. As above, the linear components of the received echo signals can be removed by pulse inversion processing.

Figure 16A:
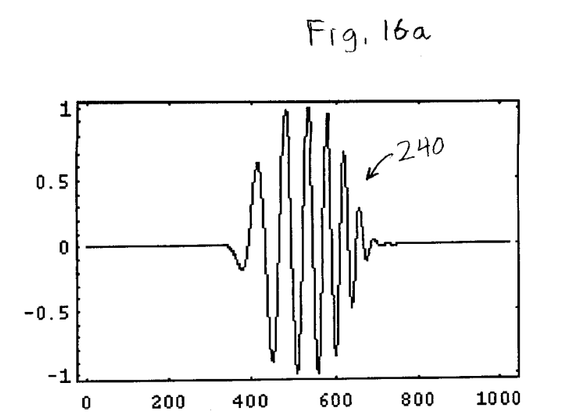
FIGS. 16a and 16b illustrate a frequency modulated multifrequency transmit pulse and the spectrum of the pulse.
Figure 16B:
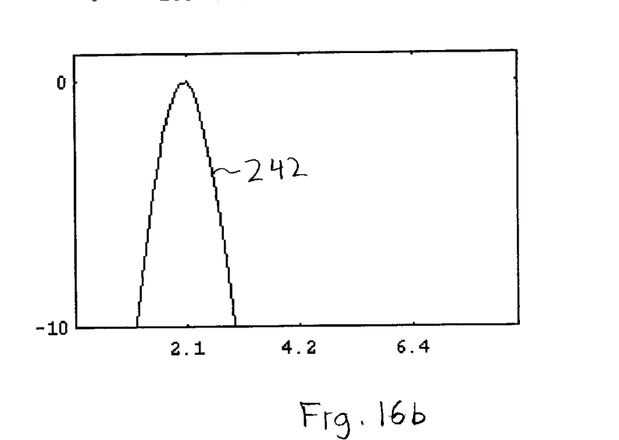

Another embodiment of the present invention is illustrated by FIGS. 16a and 16b. In this embodiment the transmit pulse is frequency modulated (an FM pulse, also known as a chirp pulse.) An acoustic pressure waveform 240 which is frequency modulated from a lower to a higher frequency is shown in FIG. 16a. The spectrum of the illustrated waveform has a nominal center frequency of 2.1 MHz as shown in FIG. 16b. The nonlinear results of interaction of the different frequency components (harmonics, sum and difference frequencies) of such a pulse can fill the complete transducer passband with echo components ranging from 1.6 to 4.0 MHz.

Figure 17:
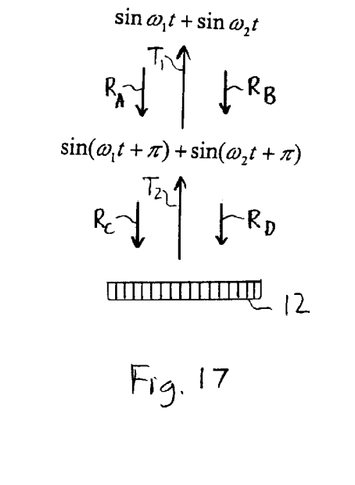
FIG. 17 illustrates the use of pulse inversion to separate sum or difference signal components from a multiline receiver.

FIG. 17 illustrates an embodiment employing multiline reception, that is, reception of multiple receive lines in response to a single transmit event, with pulse inversion separation of sum or difference signals. In this embodiment an array transducer 12 transmits a beam $T_1$ with two frequency components which is expressed as $\sin\omega_1 t + \sin\omega_2 t$. In response to this transmit beam two receive beams are produced, $R_A$ and $R_B$, which are located laterally on either side of the transmit beam $T_1$. A second multifrequency beam $T_2$ is transmitted which is out of phase with the first transmit beam and is expressed as $\sin(\omega_1 t+\pi)+\sin(\omega_2 t+\pi)$. Again, two receive beams pare produced in response to this second transmit beam which are laterally located on either side of the $T_2$ transmit beam. In the illustrated embodiment the two transmit beams are laterally spatially aligned and the receive beams are aligned on either side of the transmit beam locations. To separate the sum or difference signal components the aligned receive beams are combined by pulse inversion, that is, $R_A+R_C$ and $R_B+R_D$. Due to the phase difference of the transmit waveforms the fundamental components will cancel and the sum or difference signals will reinforce each other. In the embodiment of FIG. 17 it is seen that two spatially distinct receive scanlines of sum or difference signals have been created from two transmit events, a 1:1 correspondence and an improvement over conventional two (or higher) transmit event pulse inversion. Higher order multiline can result in even greater numbers of received scanlines per transmit event and hence even greater frame rates of display.

Figure 18:
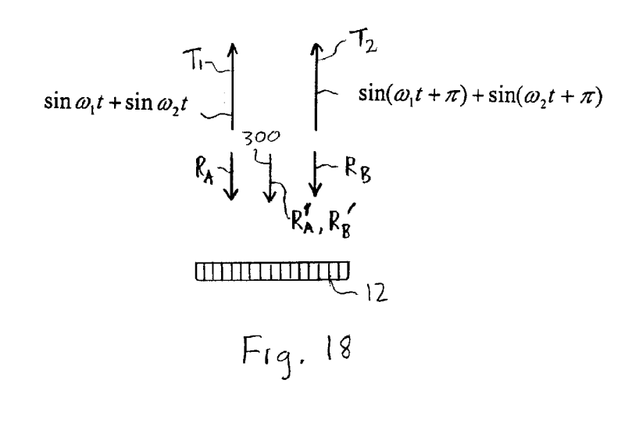
FIG. 18 illustrates the use of pulse inversion to separate sum or difference signal components using spatially distinct transmit beams.

FIG. 18 illustrates an embodiment where laterally spatially distinct transmit beams are employed to produce spatially intermediate sum or difference receive beams. A transmit beam $T_1$ of the form $\sin\omega_1 t + \sin\omega_2 t$ is first transmitted and a beam $R_A$ is received which is in alignment with the $T_1$ transmit beam. A second transmit beam $T_2$ of the form $\sin(\omega_1 t+\pi)+\sin(\omega_2 t+\pi)$ is transmitted at a spatially distinct location along the aperture of the transducer 12 and a beam $R_B$ is received in alignment with the second transmit. The two receive beams $R_A$ and $R_B$ are combined by pulse inversion $(R_A+R_B)$ to form a receive beam of sum or difference signal components at an intermediate spatial location indicated at 300. A succession of laterally spaced transmit beams which alternate in phase as shown by $T_1$ and $T_2$ can be used to produce separated sum or difference scanlines between each pair of transmit beam locations, thereby resulting in approximately a 1:1 ratio of transmit beams to separated sum or difference scanlines.

Instead of receiving beams $R_A$ and $R_B$ in alignment with the transmit beams as previously discussed, the received beams can be steered to the same intermediate location as shown by co-aligned beams $R_A'$ and $R_B'$ in FIG. 18. The two receive beams are then combined by pulse inversion to produce the sum or difference signal scanline at the intermediate location. It will further be appreciated that multiline reception can be used to receive two or more beams on either side of transmit beams $T_1$ and $T_2$ in FIG. 18 followed by pulse inversion separation of sum or difference signals, resulting in an even greater ratio of received scanlines to transmit beams and an even greater display frame rate.

I have described a nonlinear imaging technique which uses both the high and low end of the transducer bandwidth for excitation and listens (receives) at the center of the passband where sensitivity is greatest. The received bandwidth is effectively increased by listening at both the second harmonic and the difference frequency. Narrower bandwidths may be used for excitation so that more energy is delivered to a target for better signal-to-noise characteristics without sacrificing the resolution afforded by multi-component received echo signals. The principles of the present invention are fully applicable to three dimensional imaging, where sum or difference signal components and/or harmonic components are produced from insonification of a volumetric region.

What is claimed is:

1. An ultrasonic diagnostic imaging system for sum or difference frequency imaging comprising:
    a transducer array exhibiting a passband encompassing the frequencies of two different transmit frequency components and the frequency of an intermodulation product of the two different transmit frequency components;
    a transmitter including a digital waveform generator having an output which produces a digital transmit waveform having two different transmit frequency components, and a digital to analog converter having an input coupled to the output of the digital waveform generator and an output coupled to the transducer array;
    a beamformer coupled to the transducer array which produces coherent echo signals of an intermodulation product of the two different transmit frequency components; and
    an image processor, coupled to the beamformer, which produces ultrasonic image signals in response to intermodulation product echo signals.

2. The ultrasonic diagnostic imaging system of claim 1, wherein the image processor further comprises a pulse inversion processor which separates intermodulated signal components of received echo signals from fundamental frequency components.

3. The ultrasonic diagnostic imaging system of claim 1, wherein the transmitter further comprises a transmit signal weighting processor which applies selected weighting factors to the two different transmit frequency components of the transmit waveform.

4. The ultrasonic diagnostic imaging system of claim 1, wherein the transmitter further comprises a control signal input responsive to a signal selecting the frequencies of the two different transmit frequency components.

5. The ultrasonic diagnostic imaging system of claim 1, wherein the transmitter further comprises a control signal input responsive to a signal selecting the relative intensities of the two different transmit frequency components.

6. The ultrasonic diagnostic imaging system of claim 1, wherein the transmitter further comprises a control signal input responsive to a signal selecting the phase of a transmit signal relative to other transmit signals.

7. The ultrasonic diagnostic imaging system of claim 1, wherein the transmitter further comprises a plurality of digital waveform generators each coupled to one of a plurality of digital to analog converters,
    wherein the outputs of the digital to analog converters are coupled to different elements of the transducer array.

8. The ultrasonic diagnostic imaging system of claim 7, wherein the digital waveform generators and digital to analog converters are responsive to timing control signals for actuating the elements of the transducer array at the times required to transmit a steered and focused ultrasonic beam.

9. The ultrasonic diagnostic imaging system of claim 1, wherein the digital waveform generator comprises first and second digital waveform processing paths each producing a digital waveform for a different transmit frequency component at an output, and a digital combiner coupled to the processing paths which produces a multifrequency digital transmit waveform at an output,
    wherein the input of the digital to analog converter is coupled to the output of the digital combiner.

10. The ultrasonic diagnostic imaging system of claim 9, wherein each digital waveform processing path further comprises a transmit signal weighting processor which applies a selected weighting factor to digital waveform produced by the path,
    wherein the weighting factors of the two paths have a predetermined relationship.

11. The ultrasonic diagnostic imaging system of claim 10, wherein the transmitter further comprises a plurality of digital waveform generators each coupled to one of a plurality of digital to analog converters,
    wherein the outputs of the digital to analog converters are coupled to different elements of the transducer array.

12. The ultrasonic diagnostic imaging system of claim 1, wherein the digital waveform generator comprises a digital waveform library containing a plurality of digital transmit waveforms; a digital register coupled to receive a digital transmit waveform from the digital waveform library and having an output,
    wherein the input of the digital to analog converter is coupled to the output of the digital register.

13. The ultrasonic diagnostic imaging system of claim 12, further comprising a transmit signal weighting processor coupled to the digital waveform library which applies a selected weighting factor to a digital transmit waveform.

14. The ultrasonic diagnostic imaging system of claim 12, wherein the digital register is responsive to a clock signal which causes the transmitter to produce a multifrequency transmit waveform at a predetermined time.

15. The ultrasonic diagnostic imaging system of claim 14, wherein the transmitter further comprises a plurality of digital waveform generators each coupled to one of a plurality of digital to analog converters;
    wherein the outputs of the digital to analog converters are coupled to different elements of the transducer array; and wherein the timing of the clock signal causes the elements of the transducer array to be actuated at times required to transmit a steered and focused ultrasonic beam.

16. An ultrasonic diagnostic imaging system for sum or difference frequency imaging comprising:

a transducer array exhibiting a passband encompassing the frequencies of two different transmit frequency components and the frequency of an intermodulation product of the two different transmit frequency components;

a transmitter including first and second waveform processing paths each producing a digital waveform exhibiting a respective transmit frequency component at an output, and a digital combiner coupled to the waveform processing paths which produces a multifrequency digital transmit waveform at an output, and a digital to analog converter having an input coupled to the output of the digital combiner and an output coupled to the transducer array;

a beamformer coupled to the transducer array which produces coherent echo signals of an intermodulation product of the two different transmit frequency components; and an image processor, coupled to the beamformer, which produces ultrasonic image signals in response to intermodulation product echo signals.

17. The ultrasonic diagnostic imaging system of claim 16, wherein the transmitter further comprises a plurality of digital to analog converters coupled to receive multifrequency digital transmit waveforms and each having an output, wherein the outputs of the digital to analog converters are coupled to different elements of the transducer array.

18. The ultrasonic diagnostic imaging system of claim 17, wherein the intermodulation product comprises a difference frequency signal.

19. The ultrasonic diagnostic imaging system of claim 17, wherein the intermodulation product comprises a sum frequency signal.

20. An ultrasonic diagnostic imaging system for sum or difference frequency imaging comprising:

a transducer array exhibiting a passband encompassing the frequencies of two different transmit frequency components and the frequency of an intermodulation product of the two different transmit frequency components;

a transmitter including a digital waveform library containing a plurality of transmit waveforms, at least one of which comprises a digital waveform exhibiting two different transmit frequency components, and a digital to analog converter having an input coupled to receive a digital transmit waveform exhibiting two different transmit frequency components and an output coupled to the transducer array;

a beamformer coupled to the transducer array which produces coherent echo signals of an intermodulation product of the two different transmit frequency components; and an image processor, coupled to the beamformer, which produces ultrasonic image signals in response to intermodulation product echo signals.

21. The ultrasonic diagnostic imaging system of claim 20, further comprising a digital register having an input coupled to the digital waveform library and output coupled to the input of the digital to analog converter.

22. The ultrasonic diagnostic imaging system of claim 20, wherein the transmitter further comprises a plurality of digital to analog converters each coupled to receive a digital waveform exhibiting two different transmit frequency components and each having an output, wherein the outputs of the digital to analog converters are coupled to different elements of the transducer array.

23. The ultrasonic diagnostic imaging system of claim 22, wherein the intermodulation product comprises a difference frequency signal.

24. The ultrasonic diagnostic imaging system of claim 22, wherein the intermodulation product comprises a sum frequency signal.

* * * * *